United States Patent
Hoeft

(10) Patent No.: US 9,313,960 B1
(45) Date of Patent: Apr. 19, 2016

(54) INBRED SUNFLOWER LINE PH1023B

(71) Applicant: PIONEER HI BRED INTERNATIONAL INC, Johnston, IA (US)

(72) Inventor: Eric Hoeft, Davis, CA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 0 days.

(21) Appl. No.: 14/467,354

(22) Filed: Aug. 25, 2014

(51) Int. Cl.
| | |
|---|---|
| *A01H 5/10* | (2006.01) |
| *C12N 5/14* | (2006.01) |
| *A01H 5/02* | (2006.01) |
| *A01H 1/02* | (2006.01) |
| *C12N 15/82* | (2006.01) |

(52) U.S. Cl.
CPC .. *A01H 5/02* (2013.01); *A01H 1/02* (2013.01); *A01H 5/10* (2013.01); *C12N 15/8241* (2013.01)

(58) Field of Classification Search
None
See application file for complete search history.

(56) References Cited

U.S. PATENT DOCUMENTS

2011/0197297 A1* 8/2011 Benson et al. ............... 800/260

OTHER PUBLICATIONS

Record of Invoice for first sale of hybrid seed PH4ME01, Jan. 14, 2014.

* cited by examiner

*Primary Examiner* — Brent T Page
*Assistant Examiner* — Matthew Keogh
(74) *Attorney, Agent, or Firm* — Pioneer Hi-Bred Int'l, Inc.

(57) ABSTRACT

An inbred sunflower line, designated PH1023B, the plants, plant parts and seeds of inbred sunflower line PH1023B are provided. A sunflower plant, such as an inbred or hybrid, can be produced by crossing the inbred sunflower line PH1023B with itself or with another sunflower plant. Inbred and hybrid sunflower seeds and plants produced by crossing the inbred line PH1023B with another sunflower line or plants are provided. Methods for producing a sunflower plant such as inbred line PH1023B containing in its genetic material one or more transgenes and to the transgenic sunflower plants produced by that method are also disclosed. Inbred sunflower lines derived from the inbred sunflower line PH1023B, methods for producing other inbred sunflower lines derived from inbred sunflower line PH1023B, and the inbred sunflower lines derived by the use of those methods are further described.

20 Claims, No Drawings

INBRED SUNFLOWER LINE PH1023B

FIELD OF THE INVENTION

This invention is in the field of sunflower breeding, relating to an inbred sunflower line designated PH1023B.

BACKGROUND

Sunflower (*Helianthus annuus*) oil is a major edible oil worldwide. The oil component of sunflower seeds typically contributes about 80 percent of the value of a sunflower crop and is mostly used as a cooking medium. Sunflower oil is also used as salad oil, as well as in the manufacture of margarine, soap, shortening, lubricants, and as a source for biodiesel fuels. In the United States, approximately 1-2 million acres are planted in sunflowers annually, primarily in the Dakotas.

An objective of plant breeding is to combine in a single variety or hybrid various desirable traits. Objectives in sunflower breeding include improved seed yield, earlier maturity, shorter plant height, uniformity of plant type, and disease and insect resistance. High oil percentage is desirable when breeding oilseed sunflower types, whereas large seed size, a high kernel-to-hull ratio, and uniformity in seed size, shape, and color are valued in breeding and selection of nonoilseed sunflower. Other characteristics such as improved oil quality, protein percentage and protein quality are also valued.

Sunflower (*Helianthus annuus* L.), can be bred by both self-pollination and cross-pollination techniques. The sunflower head (inflorescence) usually is composed of about 1,000 to 2,000 individual disk flowers joined to a common base (receptacle). The flowers around the circumference are ligulate ray flowers with neither stamens nor pistil. The remaining flowers are hermaphroditic and protandrous disk flowers. The sunflower seed, botanically referred to as an "achene," is composed of the pericarp and embryo Natural pollination of sunflower occurs with the appearance of a tube partly exerted from the sympetalous corolla. The tube is formed by the five syngenesious anthers, and pollen is released on the inner surface of the tube. The style lengthens rapidly and forces the stigma through the tube. The two lobes of the stigma open outward and are receptive to pollen but out of reach of their own pollen initially. Although this largely prevents self-pollination of individual flowers, flowers are exposed to pollen from other flowers on the same head by insects, wind, and gravity. Both cross-pollination and self-pollination may occur naturally.

SUMMARY OF THE INVENTION

In one aspect, provided is a novel inbred sunflower line, designated PH1023B. Seeds of inbred sunflower line PH1023B, plants and plant parts of inbred sunflower line PH1023B, methods for producing a sunflower plant by crossing the inbred line PH1023B with itself or another sunflower line, methods for producing a sunflower plant containing in its genetic material one or more transgenes, and transgenic sunflower plants and plant parts so produced are provided. In one aspect the methods of incorporating one or more transgenes may include introgressing into inbred sunflower line PH1023B through backcross conversion or transformation.

In one aspect, inbred sunflower lines derived from inbred sunflower line PH1023B, methods for producing other sunflower lines derived from inbred sunflower line PH1023B, and inbred sunflower lines derived by use of those methods are also provided.

In one aspect, hybrid sunflower seeds, plant parts and plants produced by crossing the inbred line PH1023B or a locus conversion of inbred line PH1023B with another sunflower line are provided.

DETAILED DESCRIPTION

Inbred sunflower line PH1023B is a substantially homozygous line, and can be reproduced by planting seeds of the inbred line, growing the resulting sunflower plants under self-pollinating or sib-pollinating conditions with adequate isolation, and harvesting the resulting seed using techniques familiar to the agricultural arts. Sunflower plants described herein may be capable of expressing all or essentially all of the morphological and physiological characteristics of inbred line PH1023B, or of the morphological and physiological characteristics of Table 1. The seed of inbred sunflower line PH1023B, the plant produced from the inbred seed, the hybrid sunflower plant produced from the crossing of the inbred, hybrid seed, and various parts of the hybrid sunflower plant can be utilized for human food, livestock feed, and as a raw material in industry.

Genetic and Cytoplasmic Male Sterility

Control of male fertility in plants can be used in breeding techniques described herein. Two types of male sterility, genetic and cytoplasmic, are found in sunflower and can be used in the development of hybrid lines.

Hybrid sunflower seed can be produced by a male sterility system incorporating genetic or cytoplasmic male-sterile (CMS) inbreds.

Plant breeding methods involving genetic or cytoplasmic male sterility, or induction of male sterility by gibberellic acid, allow for complete hybridization of lines and facilitate estimating combining ability. Various tester parents and tester schemes can be used. In one aspect, general combining ability by the top cross method with chemical emasculation of the female parent with gibberellic acid may be used. This technique can use open pollinated cultivars, hybrids, and inbred lines as testers. In one aspect, monogenic male sterile line as a female parent can be used to test for general combining ability and subsequent diallel cross analysis with artificial emasculation to test for specific combining ability. In another aspect, the rapid conversion of lines to cytoplasmic male sterility can be achieved by using greenhouses and winter nurseries and subsequent hybrid seed production in isolated crossing blocks using open pollinated cultivars, synthetics, composites, or inbred lines as tester.

Methods of conferring genetic male sterility may include multiple mutant genes at separate locations within the genome that confer male sterility. Many sources of genetic male sterility are controlled by a single recessive gene. Lines of partial male sterility may be advantageous as the partial male sterile lines hybridize in crossing plots, and can be increased and easily maintained.

A cytoplasmic male sterile and fertility restorer system can be used in sunflower breeding programs for hybrid seed production. The system also can be used to develop suitable testers for evaluating inbred lines, and subsequent production of hybrid seed for testing. Lines that produce sterile progeny can be used in experimental production of hybrid seed. A stable form of cytoplasmic male sterility occurs from an interspecific cross involving *H. petiolaris* Nutt. and *H. annuus* L.

In one aspect, fertility restorer lines are developed by transferring a dominant restorer gene to an established inbred line with normal cytoplasm by backcrossing. Selected plants are crossed to a cytoplasmic male sterile line after each generation to determine if the fertility restorer genes are present. In one aspect, procedures such as self-pollination and selection of male fertile plants from commercial hybrids or planned crosses of parents having restorer genes in male sterile cytoplasm can be used. The plants will be fully male fertile if one or more restorer genes are present.

In one aspect, fertility-restorer lines having restorer genes in male sterile cytoplasm, which are resistant to downy mildew and have recessive branching are used. Recessive branching extends the period of pollen production and can be used to obtain simultaneous flowering with female lines in hybrid seed production fields. Examples of restorer lines include RHA271, RHA273, and RHA274.

Other methods for conferring male sterility can be used in developing male sterile and fertility restoring sunflowers. For example, a system of nuclear male sterility in corn is described in U.S. Pat. No. 5,432,068, the entire disclosure of which is herein incorporated by reference in its entiretly. This system may be used in sunflower and includes at least one or all of: identifying a native male fertility gene; silencing this native male fertility gene; removing the native promoter from the native male fertility gene and replacing it with an inducible promoter; inserting this genetically engineered gene into a plant; thereby creating a plant that is male sterile because the inducible promoter is not "on" resulting in the male fertility gene not being transcribed. Fertility is restored by inducing, or turning "on", the promoter, which in turn allows the gene that confers male fertility to be transcribed. Other methods which can be used include delivering into the plant a gene encoding a cytotoxic substance associated with a male tissue specific promoter, or the use of an antisense system in which an antisense construct to a male fertility gene is inserted in the plant to reduce expression of the male fertility polypeptide.

Inbred and Hybrid Sunflower

Male sterile inbreds are a factor which may be used in the production of sunflower inbreds and hybrids. The development of sunflower hybrids may include the development of homozygous inbred lines, the crossing of these lines, and the evaluation of the crosses. Pedigree breeding and recurrent selection breeding methods can be used to develop inbred lines from breeding populations.

Plant breeding techniques can include, for example, the ability to differentiate morphological and physiological characteristics, the ability to design evaluation techniques for genotypic and phenotypic traits of interest, and the ability to search out and exploit the genes for the desired traits in new or improved combinations. DNA markers such as restriction fragment length polymorphisms (RFLPs) randomly amplified polymorphic DNAs (RAPDS), simple sequence repeats (SSRs) and single nucleotide polymorphisms (SNPs) may also be used for example in selection of desirable plants. Linkages of molecular markers with agronomic traits such as downey mildew resistance, rust resistance and resistance to the parasitic plant *Orobanche cumanna* have been established in sunflower. Molecular markers may be used to analyse polynucletodies isolated from the seeds, plants, plant parts or cells described herein. Molecular markers may bind to particular regions of the genome and may correlate with other plant characteristics such as flower color, plant height and fertile period response. Sunflower molecular marker technologies such as isozyme polymorphisms, simple sequence repeats, single nucleotide polymorphisms and RFLP can be used to characterize inbred lines.

Agronomic traits useful in a hybrid combination include improved seed yield, improved seed oil percentage and oil quality, earlier maturity, shorter plant height, uniformity of plant type, disease resistance and insect resistance. In one aspect, performance for parental traits such as seed yields and pollen production may be monitored to facilitate providing parental lines in sufficient quantity and quality for hybridization. These traits have been shown to be under genetic control and can be affected by multiple genes.

Seed yield exhibits genetic variability and can be associated with other traits, such as stem fasciation, trichome length, serration of leaf margin, and chlorotic leaf color. Inbred lines which are used as parents for breeding crosses can differ in the number and combination of these genes. Many genes may affect yield with each having a relatively small effect on this trait, for example, compared to breeders' ability to measure yield differences in evaluation trials. In one aspect, the parents of the breeding cross differ at several of these loci resulting in genetic differences in the progeny large enough to faciliate development of desirable lines.

Pedigree breeding can begin with two original parents, each of which may have one or more desirable characteristics that is lacking in the other or which complements the other. Other sources can be included in the breeding population to improve the availability of desirable characteristics. Superior plants can be selfed and selected in successive generations. Self-pollination and selection over succeeding generations produces homogeneous lines from the heterozygous condition. In one aspect, five or more generations of selfing and selection is practiced: $F_1 \rightarrow F_2$; $F_2 \rightarrow F_3$; $F_3 \rightarrow F_4$; $F_4 \rightarrow F_5$, etc.

In one aspect, a single cross hybrid sunflower variety is formed from the cross of two inbred lines, each of which has a genotype that complements the genotype of the other. The hybrid progeny of the first generation is designated $F_1$, and are typically more vigorous than their inbred parents. This hybrid vigor, or heterosis, can be manifested in many polygenic traits, including increased vegetative growth and increased yield.

In one aspect, the development of a hybrid sunflower variety involves one or more of the following steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny ($F_1$). During the inbreeding process in sunflower, the vigor of the lines can decrease. Vigor is restored when two different inbred lines are crossed to produce the hybrid progeny ($F_1$). A consequence of the homozygosity and homogeneity of the inbred lines is that the hybrid between a defined pair of inbreds is the same. Once the inbreds that give a desirable hybrid have been identified, the hybrid seed can be reproduced indefinitely when the homogeneity of the inbred parents is maintained.

In one aspect, a single cross hybrid can be produced by crossing two inbred lines to produce the $F_1$ progeny. In one aspect, a double cross hybrid is produced by crossing four inbred lines in pairs (A×B and C×D) and then crossing the two $F_1$ hybrids again (A×B)×(C×D). A three-way hybrid can be produced from three inbred lines. Two inbreds can be crossed (A×B) to create an F1 hybrid, which is then crossed to a third inbred (A×B)×C. Hybrid vigor exhibited by $F_1$ hybrids can be lost in the next generation ($F_2$) such that seed from hybrid varieties is generally not suitable for planting stock.

Many traits of economic value in sunflower are under the genetic control of multiple genetic loci, and a large number of unique combinations of these genes are present in elite sunflower germplasm. In one aspect, the wild species of *Helianthus* may be used to increase genetic diversity of sunflower for further improvement.

In one aspect, biotechnology techniques may be used to improve sunflower as described herein. These techniques include embryo culture which can be used, for example, to facilitate crossing with wild species. In one aspect, non-native genes from other species such as bean, maize, and Brazil nut can be transferred into sunflower using, for example, *Agrobacterium tumefaciens*, biolistics or other transformation techniques. In one aspect, the production of double haploids by, for example, anther or microspore culture and the genetic mapping of valuable traits or genes using RFLP's may be used.

In one aspect, the amount of seed produced is increased while the susceptibility of the sunflower crop to environmental stresses is decreased. Selection and development of superior inbred parental lines for producing hybrids can be achieved by identifying and selecting genetically unique individuals that occur in a segregating population. The segregating population is the result of a combination of crossover events plus the independent assortment of specific combinations of alleles at many gene loci that results in specific genotypes. Based on the number of segregating genes, the frequency of occurrence of an individual with a specific genotype can be less than 1 in 10,000. Thus, even when the entire genotype of the parents has been characterized and the desired genotype is known, few or no individuals having the desired genotype may be found in a large $F_2$ or $S_0$ population. However, in many cases, details of the genotype of the parents and the desired genotype is not known. The interaction of the genotype with the environment can be a further unpredictable factor in plant breeding.

DEFINITIONS

In the description and examples that follow, a number of terms are used herein. In order to provide a clear and consistent understanding of the specification and claims, including the scope to be given such terms, the following definitions are provided. NOTE: ABS is in absolute terms and % MN is percent of the mean for the experiments in which the inbred or hybrid was grown. NOR (normalized) indicates values expressed as standard deviations from the mean. Ten units on the normalized scale represent one standard deviation. A score of 100 on the NOR scale equals the mean of the experiment. A score of 90 equals one standard deviation below the mean and a score of 110 denotes a value one standard deviation above the mean. These designators will follow the descriptors to denote how the values are to be interpreted. Below are the descriptors used in the data tables included herein.

EDBOT—Resistance to *Botrytis cinerea*—YES or NO
EDBR—Resistance to broomrape (*Orobanche* sp.) Y or N
EDBRAATT—Bract: attitude in relation to head—CPVO#27—1=not embracing or very slightly embracing, 2=slightly embracing, 3=strongly embracing
EDBRACOL SFL—Bract: green color of outer side—CPVO#26—3=Light, 4=Light to Medium, 5=Medium, 6=Medium to Dark, 7=Dark
EDBRALGT SFL—Bract: length of tip—CPVO#25—1=very short, 2=very short to short, 3=short, 4=short to medium, 5=medium, 6=medium to long, 7=long, 8
EDBRANCH—Plant: branching (excluding environmental branching)—CPVO#29—1=Absent, 9=Present
EDBRASHA—Bract: shape—CPVO#24—1=clearly elongated, 2=never clearly elongated nor clearly rounded, 3=clearly rounded
EDBRATYP—Plant: type of branching (as for 29)—CPVO#30—1=only basal, 2=predominantly basal, 3=overall, 4=predominantly apical, 5=only apical
EDBRPCT—Resistance to broomrape (*Orobanche* sp.) pct affected
EDBRs SFL—Resistance to broomrape (*Orobanche* sp.) Scale—1=very low affected above 60pct, 3=low 50 to 60, 5=medium 35 to 50, 7=high 11 to 35, 9=very high below 10
EDCAPBEE—Resistance to capricorn beetle Y or N
EDDISANT—Disk flower: anthocyanin coloration of stigma—CPVO#21—1=Absent, 9=Present
EDDISCOL—Disk flower: color—CPVO#20—1=yellow, 2=orange red, 3=purple
EDDISINT SFL—Disk flower: intensity of anthocyanin coloration of stigma—CPVO#22—3=Weak, 4=Weak to Medium, 5=Medium, 6=Medium to Strong, 7=Strong
EDDM100—Resistance to Downy Mildew 100—YES or NO
EDDM300—Resistance to Downy Mildew 300—YES or NO
EDDM304—Resistance to Downy Mildew 304—YES or NO
EDDM310—Resistance to Downy Mildew 310—YES or NO
EDDM314—Resistance to Downy Mildew 314—YES or NO
EDDM330—Resistance to Downy Mildew 330—YES or NO
EDDM330U—Resistance to Downy Mildew 330 US Type—YES or NO
EDDM700—Resistance to Downy Mildew 700—YES or NO
EDDM703—Resistance to Downy Mildew 703—YES or NO
EDDM704—Resistance to Downy Mildew 704—YES or NO
EDDM710—Resistance to Downy Mildew 710—YES or NO
EDDM714—Resistance to Downy Mildew 714—YES or NO
EDDM730—Resistance to Downy Mildew 730—YES or NO
EDDM770—Resistance to Downy Mildew 770—YES or NO
EDDMPCT—Resistance to Downy Mildew pct affected
EDDMs SFL—Resistance to Downy Mildew Score—1=very low affected above 60pct, 3=low 50 to 60, 5=medium 35 to 50, 7=high 11 to 35, 9=very high below 10
EDFLO SFL—Time of flowering—CPVO#14—1=very early, 2=very early to early, 3=early, 4=early to medium, 5=medium, 6=medium to late, 7=late, 8=late to very late, 9=very late
EDFLODAT—Flowering date MM/DD
EDFLODCK1—Flowering date MM/DD Check1
EDFLODCK2—Flowering date MM/DD Check2
EDHAITOP SFL—Stem: hairiness at the top—CPVO#13—1=absent or very weak, 3=weak, 5=medium, 7=strong, 9=very strong
EDHDATT SFL—Head: attitude—CPVO#32—1=horiz, 2=inclined, 3=vertical, 4=half-turned down straight stem, 5=half-turned down curved stem, 6=turned down straight stem, 7=turned down slightly curved stem, 8=turned down strongly curved stem, 9=over turned
EDHDSHSD SFL—Head: shape of grain side—CPVO#34—1=strongly concave, 2=weakly concave, 3=flat, 4=weakly convex, 5=strongly convex, 6=deformed EDHSIZE—Head: size—CPVO#33—3=small, 5=medium, 7=large
EDHYPANT SFL—Hypocotyl: anthocyanin coloration—CPVO#1—Absent=1 or Present=9
EDHYPINT SFL—Hypocotyl: intensity of anthocyanin coloration—CPVO#2—1=very weak, 2=very weak to weak, 3=weak, 4=weak to medium, 5=medium, 6=medium to strong, 7=strong, 8=strong to very strong, 9=very strong
EDLEAANG—Leaf: angle of lowest lateral veins—CPVO#11—1=acute, 2=right angle or nearly right angle, 3=obtuse
EDLEAAUR SFL—Leaf: auricules—CPVO#9—1=none or very small, 2=very small to small, 3=small, 4=small to medium, 5=medium, 6=medium to large, 7=large, 8=Large to very large, 9=very large
EDLEABLI SFL—Leaf: blistering—CPVO#5—1=absent to very weak, 2=very weak to weak, 3=weak, 4=weak to medium, 5=medium, 6=medium to strong, 7=strong, 8=strong to very strong, 9=very strong
EDLEACOL SFL—Leaf: green color—CPVO#4—3=Light Green, 4=Light to Medium, 5=Medium, 6=Medium to Dark, 7=Dark Green
EDLEACRO SFL—Leaf: shape of cross section—CPVO#7—1=strongly concave, 2=weakly concave, 3=flat, 4=weakly convex, 5=strongly convex
EDLEADIS SFL—Leaf: shape of distal part—CPVO#8—1=lanceolate, 2=lanceolate to narrow triangular, 3=narrow triangular, 4=narrow to broad triangular, 5=broad triangular, 6=broad triangular to acuminate, 7=broad triangular to round, 8=acuminate, 9=rounded
EDLEAHTI SFL—Leaf: height of the tip of the blade compared to insertion of petiole (at ⅔ height of plant)—CPVO#12—1=very low, 2=very low to low, 3=low, 4=low to medium, 5=medium, 6=medium to high, 7=high, 8=high to very high, 9=very high
EDLEASER SFL—Leaf: serration (fineness)—CPVO#6—1=very fine or isolated, 3=fine, 5=medium, 7=coarse, 9=very coarse
EDLEASIZ SFL—Leaf size—CPVO#3—1=very small, 3=small, 5=medium, 7=large, 9=very large
EDLEAWNG—Leaf: wings—CPVO#10—1=none or very weakly expressed, 2=weakly expressed, 3=strongly expressed
EDLHCHPO—Plant: natural position of highest lateral head to the central head—CPVO#31—1=below, 2=same level, 3=above
EDOLPCT—Oleic acid pct
EDOLS—Oleic Acid Percent (score)—1=below 35pct, 5=35 to 85pct
EDPHOHD—Resistance to *phomopsis* (head)—YES or NO
EDPHOPCT—Resistance to *phomopsis* pct affected
EDPHOs SFL—Resistance to *phomopsis* Score—1=very low affected above 60pct, 3=low 50 to 60, 5=medium 35 to 50, 7=high 11 to 35, 9=very high below 10
EDPHOSTE—Resistance to *phomopsis* (stem)—YES or NO
EDPLTHT—Plant height in cm
EDPLTHTCK1—Plant height in cm Check1
EDPLTHTCK2—Plant height in cm Check2
EDPLTHTs SFL—Plant: natural height (score)—CPVO#28—1=very short, 2=very short to short, 3=short, 4=short to medium, 5=medium, 6=medium to long, 7=long, 8=long to very long, 9=very long
EDPOLPRD—Disk flower: production of pollen—CPVO#23—1=Absent, 9=Present
EDRAYCOL—Ray flower: color—CPVO#19—1=yellowish white/ivory, 2=light yellow, 3=medium yellow, 4=orange yellow, 5=orange, 6=purple, 7=reddish brown, 8=multicolored
EDRAYDEN SFL—Ray flowers: density—CPVO#15—3=Sparse, 4=Sparse to Medium, 5=Medium, 6=Medium to Dense, 7=Dense
EDRAYDIS—Ray flower: disposition—CPVO#17—1=flat, 2=longitudinal recurved, 3=undulated, 4=strongly recurved to back of head
EDRAYLEN SFL—Ray flower: length—CPVO#18—3=Short, 4=Short to Medium, 5=Medium, 6=Medium to Long, 7=Long
EDRAYSHA—Ray flowers: shape—CPVO#16—1=fusiform, 2=narrow ovate, 3=broad ovate, 4=rounded
EDRUST—Resistance to rust Y or N
EDRUSTs SFL—Resistance to rust—1=very low affected above 60pct, 3=low 50 to 60, 5=medium 35 to 50, 7=high 11 to 35, 9=very high below 10
EDSCL—Resistance to *sclerotinia* (stem)—YES or NO
EDSCLHD—Resistance to *sclerotinia* (head)—YES or NO
EDSCLHDs SFL—Resistance to *sclerotinia* (head) Score—1=very low affected>60%, 3=low 50 to 60, 5=medium 35 to 50, 7=high 11 to 35, 9=very high <10
EDSCLPCT—Resistance to *Sclerotinia* pct affected
EDSCLs SFL—Resistance to *Sclerotinia* Score—1=very low affected above 60pct, 3=low 50 to 60, 5=medium 35 to 50, 7=high 11 to 35, 9=very high below 10
EDSCLsca—Resistance to *sclerotinia* (stem) scale—1=resistant, 2=moderately resistant, 3=medium susceptible, 4=medium to very susceptible, 5=very susceptible
EDSDCOL—Seed: main color—CPVO#38—1=white, 2=whitish grey, 3=grey, 4=light brown, 5=medium brown, 6=dark brown, 7=black, 8=purple
EDSDSHAP—Seed: shape—CPVO#36—1=elongated, 2=narrow ovoid, 3=broad ovoid, 4=rounded
EDSDSIZE SFL—Seed: size—CPVO#35—1=very small, 2=very small to small, 3=small, 4=small to medium, 5=medium, 6=medium to large, 7=large, 8=Large to very large, 9=very large
EDSDSPPR—Seed: spots on pericarp—1=Absent, 9=Present
EDSDSTBE—Seed: stripes between margins—CPVO#40—1=none or very weakly expressed, 2=weakly expressed, 3=strongly expressed
EDSDSTBESP trait—Seed: stripes between margins—Spain—1=none or very weakly expressed, 5=weakly expressed, 9=strongly expressed
EDSDSTCO—Seed: color of stripes—CPVO#41—1=white, 2=grey, 3=brown, 4=black
EDSDSTON—Seed: stripes on margin—CPVO#39—1=none or very weakly expressed, 2=weakly expressed, 3=strongly expressed
EDSDSTONSP trait—Seed: stripes on margin—Spain—1=none or very weakly expressed, 5=weakly expressed, 9=strongly expressed
EDSDSTRI—Seed: stripes—1=Absent, 9=Present
EDSDTHIC SFL—Seed: thickness relative to size—CPVO#37—3=Thin, 4=Thin to Medium, 5=Medium, 6=Medium to Thick, 7=Thick
EDSNMOT—Resistance to Snout Moth (Pyralidae) (ent.)—YES or NO
50PFLW—The number of days it takes for 50 percent of the plants to reach the stage of R5.1 R5.1 is when the ray flowers are visible and the first ring of disk flowers has emerged and flowered.

ALBSC—*Albugo* (*Albugo tragopogonis*) resistance (1-9 scale; 9=fully resistant, 1=fully susceptible)

ALTSC—*Alternaria* (*Alternaria helianthi*) resistance (1-9 scale; 9=fully resistant, 1=fully susceptible)

BOTSC—*Botrytis* (*Botrytis cinerea*) resistance (1-9 scale; 9=fully resistant, 1=fully susceptible)

BRMESC—Broomrape (*Orobanche cumana*) Race E resistance (1-9 scale; 9=fully resistant, 1=fully susceptible)

BRMHSC—Broomrape (*Orobanche cumana*) Race H resistance (1-9 scale; 9=fully resistant, 1=fully susceptible)

CHRRSC—Charcoal Rot (*Macrophomina phaseolina*) resistance (1-9 scale; 9=fully resistant, 1=fully susceptible)

CTRSSC=A 1 to 9 visual rating indicating the degree of seed set obtained within the sunflower head. A 1 equals a head where only the outer 10% of the head sets seed. A 9 equals a head where 90-100% of the head sets seed.

CYTOPLASMIC MALE STERILE (CMS) PLANT OR INBRED LINE. A sunflower line that produces no viable pollen is called male sterile. Male sterility is inherited maternally, i.e. the male sterile plant is used as the female parent in a cross with pollen from another sunflower. CMS lines are produced by crossing a maintainer line with a sunflower plant with the cytoplasmic male sterility trait and then backcrossing to the maintainer line until a male sterile line that is homologous to the maintainer line in all other respects is developed. CMS lines are also referred to as female lines.

DNY304CC—Downy Mildew (*Plasmopara halstedii*) Race 304 resistance (1-9 scale; 9=fully resistant, 5=segregating, 1=fully susceptible)

DNY334CC—Downy Mildew (*Plasmopara halstedii*) Race 334 resistance (1-9 scale; 9=fully resistant, 5=segregating, 1=fully susceptible)

DNY710CC—Downy Mildew (*Plasmopara halstedii*) Race 710 resistance (1-9 scale; 9=fully resistant, 5=segregating, 1=fully susceptible)

DNY714CC—Downy Mildew (*Plasmopara halstedii*) Race 714 resistance (1-9 scale; 9=fully resistant, 5=segregating, 1=fully susceptible)

DYSR9=The number of days it takes for 50 percent of the plants to reach the R9 developmental stage. This is a stage of physiological maturity that is determined when the back of the flowering head has reached a yellowing stage and the outer bracts of the head have started to brown. This normally is a stage when the seed moisture is at about 30-40% moisture.

HDSSC=Head shape score. Indicates head shape (1=closed "midge" ball, 2=trumpet, 3=clam, 4=concave, 5=cone, 6=reflex, 7=distorted, 8=convex, 9=flat).

MDGSC=Resistance to the sunflower midge, *Contarinia schulzi*, based on head deformation. Rated on a 1-9 scale, 9=no head deformation (fully resistant), 5=moderate head deformation, 1=severe head deformation (fully susceptible).

MST=This is a measure of seed moisture taken at harvest time. It is recorded in percentage of moisture to seed weight.

OIL10P=The percentage of oil content measured from the harvested grain adjusted to a 10% moisture level.

OILYLD=Oil yield in quintals per hectare, calculated based on grain yield and dry weight grain oil percentage.

PHOSC=*Phompsis* stalk rot (*Phompsis helianthii*) resistance (1-9 scale; 9=fully resistant, 1=fully susceptible)

PLTHT=This is the height of the head at flowering, measured in decimeters.

PMASC=*Phoma* stalk rot (*Phoma macdonaldii*) resistance (1-9 scale; 9=fully resistant, 1=fully susceptible)

QU/HA=Yield in quintals per hectare.

R160=A measure of the percentage of Palmitic acid found in the oil of the seed as measured by a rapid reading from a gas chromatograph.

R180=A measure of the percentage of Stearic acid found in the oil of the seed as measured by a rapid reading from a gas chromatograph.

R181=A measure of the percentage of Oleic acid found in the oil of the seed as measured by a rapid reading from a gas chromatograph.

R182=A measure of the percentage of Linoleic acid found in the oil of the seed as measured by a rapid reading from a gas chromatograph.

RESTORER LINE. A line possessing the gene or genes to restore male fertility or viable pollen to a sunflower hybrid or inbred line and progeny having a maternal cytoplasm that conditions male sterility. This term is also discussed in the literature. See for e.g. Fick, "Breeding and Genetics," in Sunflower Science and Technology 279-338 (J. F. Carter ed. 1978), the contents of which are incorporated herein by reference.

RHZSC=Resistance to *Rhizopus* head rot. Rating scale from 1-9. Higher scores indicate greater resistance.

RLGSC=A 1 to 9 visual rating indicating the level of root lodging. The higher the score the less root lodging that occurs.

RSTSC=Black Rust (*Puccinia helianthi*) resistance (1-9 scale; 9=fully resistant, 1=fully susceptible)

SCLHSC=*Sclerotinia* Head Rot (*Sclerotinia sclerotiorum*) resistance (1-9 scale; 9=fully resistant, 1=fully susceptible)

SCLRSC=*Sclerotinia* Basal Root Rot (*Sclerotinia sclerotiorum*) resistance (1-9 scale; 9=fully resistant, 1=fully susceptible)

SDVSC=Seedling vigor score. 1-9 visual rating taken. Higher scores indicate more seedling vigor (early growth).

SEPSC=*Septoria* Leaf Spot (*Septoria helianthi*) resistance (1-9 scale; 9=fully resistant, 1=fully susceptible)

SLFFSC=SLFFER. A 1 to 9 visual rating indicating the degree of self fertility found within a self pollinated head. A score of 1 indicates <10% of the seed sets under a bagged self. A score of 9 indicates that 90-100% of the seed sets under a bagged self.

STYGRN=STAY GREEN. Stay green is the measure of plant health near the time of physiological maturity. A high score indicates better late-season plant health.

SUNFLOWER SEED. Botanically referred to as an "achene", comprised of the pericarp and embryo.

TSTWT=Test weight of seed measured in kilograms per hectoliter.

VERWSC=*Verticillium* wilt (*Verticillium dahliae*) resistance (1-9 scale; 9=fully resistant, 1=fully susceptible)

In one aspect, a method for producing inbred PH1023B includes the steps of planting a collection of seed comprising seed of a hybrid, one of whose parents is inbred PH1023B, growing plants from the collection of seed, identifying the inbred PH1023B plants, selecting the inbred PH1023B plant, and controlling pollination in a manner which preserves the homozygosity of the inbred PH1023B plant. The collection of seed can also include seed of the inbred PH1023B.

Inbred sunflower line PH1023B may be used as a male or female in the production of the first generation F1 hybrid. Inbred sunflower line PH1023B has a relative maturity of approximately 93 days. The variety has shown uniformity and stability within the limits of environmental influence for all the traits as described in the Variety Description Information (See Table 1). The variety has been self-pollinated a sufficient number of generations with attention paid to uniformity of plant type to ensure the homozygosity and phenotypic stability necessary for use in commercial hybrid seed production. The variety has been increased both by hand and in isolated fields with continued observation for uniformity. No variant traits have been observed or are expected in inbred sunflower line PH1023B. Inbred sunflower line PH1023B contributes to high yield hybrids for seed and oil content. PH1023B is resistant to tribenuron-methyl.

Inbred sunflower lines disclosed herein can be used in the production of hybrid sunflower lines and are preferably highly homogeneous, homozygous and reproducible for the production of commercial hybrids. One analytical method that can be used to determine the homozygotic and phenotypic stability of inbred lines is the observation of phenotypic traits, for example, from data collected in field experiments over the life of the sunflower plant. Phenotypic characteristics most often observed include traits associated with plant morphology, flower morphology, insect and disease resistance, maturity, and yield.

In one aspect, a method for producing a PH1023B-derived sunflower plant includes the steps of crossing inbred sunflower line PH1023B with a second sunflower plant to yield progeny sunflower seed, and growing the progeny sunflower seed under plant growth conditions to yield the PH1023B-derived sunflower plant. The method can further include crossing the PH1023B-derived sunflower plant with itself or another sunflower plant to yield additional PH1023B-derived progeny sunflower seed, growing the progeny sunflower seed under plant growth conditions, to yield additional PH1023B-derived sunflower plants, and, optionally repeating the crossing and growing steps at least 1, 2, 3, 4, 5, 6, 7, 8, 9 or 10 times and less than 10, 9, 8, 7, 6, 5, 4, 3, 2 times to generate further PH1023B-derived sunflower plants. The method can further include utilizing plant tissue culture methods to produce progeny of the PH1023B-derived sunflower plant. Sunflower plants, plant parts, or plant cells produced by this method and progeny of the PH1023B-derived sunflower plant obtained utilizing plant tissue culture methods described herein, are also provided.

The genotype of a plant can be examined, for example, by a laboratory-based technique such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNP's).

Inbred sunflower line PH1023B is an express resistant, oleic oil type maintainer line. Hybrids produced from inbred PH1023B are well-adapted to the Northern Plains region of the United States and the Central, Eastern, and Western regions of Europe.

PH1023B derives from the cross T0243HG*3/B0503HG. T0243HG and B0503HG are both proprietary lines of Pioneer Hi-Bred International, Inc. The backcross and pedigree methods were used in the development of PH1023B. PH1023B is a bulk of BC2F6 seed tracing back to a single BC2F5 selection. The sterile analog derives from the CMS PET1 cytoplasm following 5 generations of backcrossing. It is homozygous dominant for single heads.

The inbred has shown uniformity and stability within the limits of environmental influence for all the traits as described above and in the Variety Description Information (Table 1) that follows. The inbred has been self-pollinated a sufficient number of generations with careful attention paid to uniformity of plant type to ensure the homozygosity and phenotypic stability necessary to use in commercial production. The line has been increased both by hand and in isolated fields with continued observation for uniformity. No variant traits have been observed or are expected in PH1023B.

Inbred sunflower line PH1023B, being substantially homozygous, can be reproduced by planting seeds of the line, growing the resulting sunflower plants under self-pollinating or sib-pollinating conditions with adequate isolation, and harvesting the resulting seed, using techniques familiar to the agricultural arts.

TABLE 1

Variety description information for inbred PH1023B (comparison variety = HA89)

| | |
|---|---|
| Market usage type: | |
| Oil (% of whole undecoricated seed) | 45.2 |
| Oleic (as % of oil) | 90.1 |
| Disease, parasite, insect, and herbicide reactions: | |
| Sulfonylurea (tribenuron-methyl) tolerance (# plants resistant/# plants susceptible) | 250/0 |
| 1. Flowering | Medium |
| 2. Maturity: | |
| No. of days to Stage R 5.1 (from emergence) | 63 days<br>1 day later than comparison variety |
| No. of days to physiological maturity (from emergence) | 93 days<br>2 days earlier than comparison variety |
| 3. Height: cm tall at harvest ripeness | 136 cm<br>30 cm taller than comparison variety |
| 4. Stem: | |
| Length of internodes at harvest ripeness compared to check in cm | 6.8 cm<br>0.4 cm longer than comparison variety |
| Branching | No branching |
| Color of growing point | Green |
| 5. Leaves: (mid-stem at flowering) | |
| Blade length | 19 cm<br>3 cm shorter than comparison variety |
| Number of leaves | 20 leaves<br>2 leaves fewer than comparison variety |
| Leaf shape | Cordate |
| Leaf apex | Acuminate |
| Leaf base | Auriculate |
| Leaf margin | Medium serrate |
| Depth of margin indentations | Deep |
| Attitude | Descending |
| Surface | Smooth |
| Color | Light Green |
| Margin color | Green |
| 6. Head at flowering: | |
| Ray flowers | Present |
| Ray flower color | Yellow |
| Disk flower color | Yellow |
| Anthocyanin in stigmas | Absent |
| Pollen color | Light yellow |
| Pappi color | Green |
| Ray length in mm | 54 mm<br>6 mm shorter than comparison variety |
| Ray width in mm | 15 mm<br>2 mm shorter than comparison variety |
| Ray appearance | Flat |
| 7. Head at seed maturity | |
| Diameter in cm | 13 cm<br>1 cm wider than comparison variety |
| Receptacle shape | Flat |
| Head (neck) attitude | Descending |

TABLE 1-continued

Variety description information for inbred PH1023B
(comparison variety = HA89)

| | |
|---|---|
| 8. Seeds: | |
| Outer pericarp | Striped black |
| Middle pericarp | White |
| Inner pericarp (seed coat) | No color |
| Stripes | Narrow dark-gray striping |
| Position of stripes if present | Both (lateral and marginal) |
| Shape | Oblong |
| Shape (cross section) | Curved |
| Length in mm | 12 mm |
| | 2 mm longer than comparison variety |
| Grams/100 seeds | 5.6 |
| | 0.4 gm lighter than comparison variety |

Performance Examples of PH1023B

In the examples below, the traits and characteristics of inbred sunflower line PH1023B are presented in its hybrid combination with Pioneer male line PH5015R. The hybrid combination of PH1023B/PH5015R is denoted P64ME01. The data collected on P64ME01 is presented for the key characteristics and traits.

Table 2 is a paired comparison report which compares Pioneer Hi-Bred Sunflower hybrid P64ME01 and Pioneer Hi-Bred proprietary Sunflower hybrid P63ME80. The results indicate that the P64ME01 hybrid is significantly higher yielding with a significantly higher income per hectare than the P63ME80 hybrid. The P64ME01 hybrid also demonstrates a significantly higher oil yield than the P63ME80 hybrid. The P64ME01 hybrid further shows significantly greater resistance to *orobanche cumanna* as evidenced by the data reflected in the BRMESC column

TABLE 2

PAIRED COMPARISON REPORT YIELD AND OIL YIELD GIVEN IN LBS/ACRE
VARIETY #1 - P64ME01
VARIETY #2 - P63ME80

| | GE Name | YIELD | HRVWT | MST | PLTHT | TSTWT | OILYLD |
|---|---|---|---|---|---|---|---|
| VAR 1 | P64ME01 | 2569.0325 | 11.2454 | 9.518 | 18.1354 | 28.5602 | 771.1806 |
| VAR 2 | P63ME80 | 2303.0044 | 9.9771 | 8.6015 | 17.7698 | 29.2722 | 669.7536 |
| Diff | | 266.0281 | 1.2683 | 0.9165 | 0.3656 | −0.712 | 101.427 |
| Adv % | | 11.5513 | 12.7121 | 10.6551 | 2.0574 | −2.4323 | 15.1439 |
| SE XF | | 60.1042 | 0.2671 | 0.2336 | 0.3247 | 0.589 | 39.0815 |
| Loc # | | | | | | | |
| XF | | 10 | 10 | 10 | 4 | 10 | 4 |
| z | | 4.42611498 | 4.748408836 | 3.92337 | 1.125962427 | −1.2088 | 2.595269 |
| Prob | | <0.0001 | <0.0001 | <0.0001 | 0.1303 | 0.1133 | 0.0047 |

| | GE Name | 50PFLW | BRMESC | BRMRSC | DW OIL | HARHT | HD SCL |
|---|---|---|---|---|---|---|---|
| VAR 1 | P64ME01 | 74.7974 | 8 | 6 | 39 | 17 | 69 |
| VAR 2 | P63ME80 | 73.1828 | 3 | 4 | 40 | 16 | 72 |
| Diff | | 1.6146 | 5 | 2 | −1 | 2 | −3 |
| Adv % | | 2.2063 | 132 | 51 | −3 | 10 | −4 |
| SE XF | | 0.2748 | 1 | 1 | 1 | 0 | 5 |
| Loc # | | | | | | | |
| XF | | 15 | 1 | 2 | 5 | 4 | 3 |
| z | | 5.87555 | 5 | 2 | −1 | | −0.6 |
| Prob | | <0.0001 | <0.0001 | 0.0228 | 0.1587 | | 0.2743 |

| | GE Name | HDSCNT | OIL10P | PCTPHO | PHOCNT | RT SCL | RTSCNT |
|---|---|---|---|---|---|---|---|
| VAR 1 | P64ME01 | 6 | 37 | 88 | 3 | 65 | 5 |
| VAR 2 | P63ME80 | 6 | 38 | 81 | 5 | 47 | 8 |
| Diff | | 1 | −1 | 7 | −2 | 18 | −3 |
| Adv % | | 17 | −3 | 9 | −40 | 39 | −33 |
| SE XF | | 1 | 1 | 5 | 1 | 5 | 1 |
| Loc # | | | | | | | |
| XF | | 3 | 5 | 3 | 3 | 2 | 2 |
| z | | 1 | −1 | 1.4 | −2 | 3.6 | −3 |
| Prob | | 0.1587 | 0.1587 | 0.0808 | 0.0228 | 0.0002 | 0.0013 |

TABLE 1-continued

Variety description information for inbred PH1023B
(comparison variety = HA89)

| | |
|---|---|
| Percent held on 7.9 mm (20/64) round-hole screen | 0 |

In one embodiment, methods for producing a sunflower plant by crossing a first parent sunflower plant with a second parent sunflower plant are provided wherein either the first or second parent sunflower plant is an inbred sunflower plant of the line PH1023B or is a transformed plant of the line PH1023B. In one embodiment, both first and second parent sunflower plants are of the inbred sunflower plant line PH1023B, a transformed plant of the line PH1023B or a combination thereof. Methods are provided for producing an inbred sunflower line PH1023B-derived sunflower plant by crossing inbred sunflower line PH1023B or a transformed plant of the line PH1023B with a second sunflower plant, growing the progeny seed, and repeating the crossing and growing steps with the inbred sunflower line PH1023B-derived plant from 0 to 1, 2, 3, 4 or 5 or more times. Methods may include using the inbred sunflower line PH1023B such as, for example, by selfing, backcrosses, hybrid production, crosses to populations, and the like. All plants produced using inbred sunflower line PH1023B as a parent are within the scope of this invention, including plants derived from inbred sunflower line PH1023B. Advantageously, the inbred sunflower line is used in crosses with other, different sunflower inbreds to produce first generation ($F_1$) sunflower hybrid seeds in plants with superior characteristics.

It should be understood that the inbred, whether transformed or non-transformed, can, through routine manipulation of cytoplasmic or other factors, be produced in the male sterile form. Such embodiments are also contemplated within the scope of the present claims. The foregoing was set forth by way of example and is not intended to limit the scope of this invention.

As used herein the term plant part includes plant cells, plant protoplasts, plant cell tissue cultures from which sunflower plants can be regenerated, plant calli, plant clumps and plant cells that are intact in plants, or parts of plants, such as embryos, pollen, ovules, flowers, leaves, seeds, stems, stalks, cortex, pith, involucral bracts, ray flowers, disk flowers, achene, interfloral bracts, receptacle, stigma, anther, style, filament, calyx, seed, seed coat, endosperm, embryo, roots, root tips, anthers, silk and the like.

In one embodiment, plants or plantlets can be regenerated from sunflower callus, such as isolated stem pithum and callus. Standard tissue culture variables such as methods of staging and preparation of explants, composition of culture media, cultural conditions, timing of the regeneration process, plant establishment, and maintenance of fertility can also be used in the compositions and methods described herein. Explant sources which may be used include, without limitation, one or more of seedling hypocotyl, mature cotyledon, immature cotyledon, immature embryo-somatic embryogenesis, immature embryo-rescued, primary leaflets, meristem, embryonic axis, half apex, unfertilized ovary or ovule, anther, microspore, shoot-tip protoplasts, hypocotyl protoplasts, hypocotyl and cotyledon protoplasts. Suitable explants for culture initiation and plant regeneration include one or more of mature cotyledons, immature embryos, hypocotyls and excised meristems. In one embodiment, a sunflower plant is regenerated from the tissue culture of sunflower line PH1023B, which may be capable of expressing all the morphological and physiological characteristics of inbred line PH1023B or the characteristics listed in Table 1. A detailed description of culture systems for *Helianthus annuus* known in the art can be found in Chapter 11, Sunflower Biotechnology, Bidney, D. L. and Scelonge, C. J., pp. 559-593 and references cited therein. Sunflower Technology and Production, edited by A. A. Schneiter, Agronomy 35, publishers, American Society of Agronomy Inc. 1997.

Locus Conversion and Transformation of Sunflower

In one aspect, the sunflower genome is engineered to contain and express foreign, non-native or heterologous genes or coding sequences, or additional, or modified versions of native or endogenous genes or coding sequences (for example driven by different promoters) in order to alter the traits of a plant in a specific manner. A coding sequence is a nucleic acid or polynucleotide that encodes a polypeptide. Such foreign, additional and/or modified genes or coding sequences are referred to herein collectively as "transgenes". A locus conversion refers to plants within a variety that have been modified in a manner that retains the overall genetics of the variety and further comprises one or more loci with a specific desired trait, such as male sterility, insect control, disease control or herbicide tolerance. Examples of single locus conversions include mutant genes, transgenes and native traits finely mapped to a single locus. One or more locus conversion traits may be introduced into a single sunflower variety. In particular embodiments, versions of the claimed sunflower line PH1023B which contain at least 1, at least 2, at least 3 at least 4, at least 5, at least 5, at least 7, at least 8, at least 9 or at least 10 or more transgenes or locus conversions and less than 50, less than 40, less than 30, less than 25, less than 20, less than 15, less than 10, less than 9, less than 8 and less than 7, less than 6, less than 5, less than 4, less than 3 or less than 2 transgenes or locus conversions are provided. Methods of introducing at least 1, at least 2, at least 3 at least 4, at least 5, at least 5, at least 7, at least 8, at least 9 or at least 10 and less than 50, less than 40, less than 30, less than 25, less than 20, less than 15, less than 10, less than 9, less than 8 and less than 7, less than 6, less than 5, less than 4, less than 3 or less than 2 transgenes or locus conversions are provided. The transgenes or locus conversions may be multiple copies of the same polynucleotide or coding sequence, may be different polynucleotides or coding sequences, or may be a combination thereof. In certain embodiments, increasing or decreasing expression of a transgene, ectopically expressing a transgene, or a combination thereof results in plants with altered traits, such as one or more of herbicide resistance, insect resistance, tolerance to abiotic or biotic stress, such as drought, improved standability or other traits described herein. The transgenes or locus conversions may be operably linked to one or more regulatory elements.

A method for producing a sunflower plant that contains in its genetic material one or more transgenes or locus conversions can include the steps of crossing a PH1023B sunflower plant comprising a transgene or locus conversion with a plant of another sunflower line, or a non-transformed or differently transformed sunflower plant of the line PH1023B, such that the genetic material of the progeny of the cross contains the one or more transgenes. Sunflower plants, plant parts, or plant cells produced by the method are also envisaged.

As used herein, "polynucleotide" includes reference to a deoxyribonucleotide or ribonucleotide polymer in either single- or double-stranded form and can, in certain embodiments, be includes in a polynucleotide construct or nucleotide construct for us in the methods and plants described herein. The use of the terms "polynucleotide constructs" or "nucleotide constructs" herein is not intended to limit the present invention to nucleotide constructs comprising DNA. Polynucleotide constructs and oligonucleotides composed of ribonucleotides and combinations of ribonucleotides and deoxyribonucleotides, may also be employed in the methods disclosed herein. The nucleotide constructs, nucleic acids, and nucleotide sequences of the invention additionally encompass all complementary forms of such constructs, molecules, and sequences.

In one embodiment, an expression vector which will function in plant cells is introduced into a plant cell. Such a vector comprises DNA comprising a gene or coding sequence under control of or operably linked to a regulatory element, for example, a promoter, a terminator or a combination thereof. As used herein, a polynucleotide, gene or coding sequence is "operably linked" when it is placed into a functional relationship with a second polynucleotide sequence. For instance, a promoter is operably linked to a coding sequence if the promoter is connected to the coding sequence such that it may effect transcription of the coding sequence. In various embodiments, the polynucleotides, genes or coding sequences may be operably linked to at least one, at least two, at least three, at least four, at least five, or at least ten promoters. The expression vector may contain 1, 2, 3, 4, 5, 6, 7, 8, 9, or 10 or more and less than 20, 15, 10, 9, 8, 7, 6, 5, 4, 3, or 2 such operably linked gene/regulatory element combinations. The vector(s) may be in the form of a plasmid, and can be used, alone or in combination with other plasmids, to provide transformed sunflower plants, using transformation methods as described herein to incorporate transgenes into the genetic material of the sunflower plant(s).

Expression Vectors for Sunflower Transformation

Marker Genes

In one aspect, expression vectors include at least one, at least two, at least three, at least four, or at least five genetic markers, operably linked to one ore more a regulatory elements, such as a promoter, that allows transformed cells containing the marker to be either recovered by negative selection, i.e. inhibiting growth of cells that do not contain the selectable marker gene, or by positive selection, i.e., screening for the product encoded by the genetic marker. Suitable selectable marker genes for plant transformation include, for example, genes that code for enzymes that metabolically detoxify a selective chemical agent such as an antibiotic or a herbicide, or genes that encode an altered target which is insensitive to the inhibitor. Positive selection methods may also be used.

Selectable marker genes or sequences which may be used include sequences which encode the neomycin phosphotransferase II (nptII), hybrimycin phosphotransferase, gentamycin acetyl transferase, streptomycin phosphotransferase, aminoglycoside-3'-adenyl transferase, the bleomycin resistance determinant, resistance to herbicides such as glyphosate, glufosinate or broxynil, mouse dihydrofolate reductase, plant 5-enolpyruvylshikimate-3-phosphate synthase and plant acetolactate synthase.

Suitable reporter genes or sequences which may be used include sequences which encode β-glucuronidase (GUS), β-galactosidase, luciferase, chloramphenicol acetyltransferase, Green Fluorescent Protein (including mutants of GFP) and a dominant constitutive regulator of the *Zea mays* anthocyanin pigmentation pathway.

Promoters

Genes or coding sequences included in expression vectors can be operably linked to a nucleotide sequence comprising a regulatory element, for example, a promoter. Several types of promoters are well known in the transformation arts, as are other regulatory elements that can be used alone or in combination with promoters. As used herein "promoter" includes reference to a region of DNA upstream from the start of transcription and which is involved in recognition and binding of RNA polymerase and other proteins to initiate transcription. In one aspect, the promoter is a heterologous promoter. A heterologous promoter includes, for example, a promoter which is different from that naturally associated with and promoting expression of the polynucleotide coding sequence, or a modified variant of the polynucleotide's own promoter. In certain embodiments, the polynucleotide sequence is provided as a construct in which a promoter is operably linked to the polynucleotide. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissues are referred to as "tissue-specific". A "cell type" specific promoter primarily drives expression in certain cell types in one or more organs, for example, vascular cells in roots or leaves.

An "inducible" promoter is a promoter which is under environmental control. Optionally, the inducible promoter is operably linked to a nucleotide sequence encoding a signal sequence which is operably linked to a gene for expression in sunflower. Tissue-specific, tissue-preferred, cell type specific, and inducible promoters constitute the class of "non-constitutive" promoters. Exemplary inducible promoters include, but are not limited to, that from the ACEI system which responds to copper (Mett et al. *PNAS* 90: 4567-4571 (1993)); In2 gene from sunflower which responds to benzenesulfonamide herbicide safeners (Hershey et al., *Mol. Gen. Genetics* 227: 229-237 (1991) and Gatz et al., *Mol. Gen. Genetics* 243: 32-38 (1994)) or Tet repressor from Tn10 (Gatz et al., *Mol. Gen. Genet.* 227: 229-237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88: 0421 (1991).

A "constitutive" promoter is a promoter which is active under most environmental conditions and may be operably linked to a gene or coding sequence for expression in sunflower or to a nucleotide sequence encoding a signal sequence which is operably linked to a gene for expression in sunflower. Exemplary constitutive promoters include, but are not limited to, the promoters from plant viruses such as the 35S promoter from CaMV (Odell et al., *Nature* 313: 810-812 (1985) and the promoters from such genes as rice actin (McElroy et al., *Plant Cell* 2: 163-171 (1990)); ubiquitin (Christensen et al., *Plant Mol. Biol* 12: 619-632 (1989) and Christensen et al., *Plant Mol. Biol.* 18: 675-689 (1992)): pEMU (Last et al., *Theor. Appl. Genet.* 81: 581-588 (1991)); MAS (Velten et al., *EMBO J.* 3: 2723-2730 (1984)) and maize H3 histone (Lepetit et al., *Mol. Gen. Genet.* 231: 276-285 (1992) and Atanassova et al., *Plant Journal* 2 (3): 291-300 (1992)). The ALS promoter, a XbaI/NcoI fragment 5' to the *Brassica napus* ALS3 structural gene (or a nucleotide sequence that has substantial sequence similarity to said XbaI/NcoI fragment), represents a particularly useful constitutive promoter. See PCT application WO96/30530.

Tissue-specific promoters operably linked to a gene or coding sequence for expression in sunflower can be used. Optionally, the tissue-specific promoter is operably linked to a nucleotide sequence encoding a signal sequence which is operably linked to a gene for expression in sunflower. Plants transformed with a gene of interest operably linked to a tissue-specific promoter produce the protein product of the transgene exclusively, or preferentially, in a specific tissue. Exemplary tissue-specific or tissue-preferred promoters include, but are not limited to, a root-preferred promoter, such as that from the phaseolin gene (Murai et al., *Science* 23: 476-482 (1983) and Sengupta-Gopalan et al., *Proc. Natl. Acad. Sci. USA* 82: 3320-3324 (1985)); a leaf-specific and light-induced promoter such as that from cab or rubisco (Simpson et al., *EMBO J.* 4(11): 2723-2729 (1985) and Timko et al., *Nature* 318: 579-582 (1985)); an anther-specific promoter such as that from LAT52 (Twell et al., *Mol. Gen. Genet.* 217: 240-245 (1989)); a pollen-specific promoter such as that from Zm13 (Guerrero et al., *Mol. Gen. Genet.* 224: 161-168 (1993)) or a microspore-preferred promoter such as that from apg (Twell et al., *Sex. Plant Reprod.* 6: 217-224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondrion, or for secretion into the apoplast, can be accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized. The signal sequence can be used to direct a polypeptide to either an intracellular organelle or subcellular compartment or for secretion to the apoplast. Useful signal sequences known in the art can be used.

Foreign Protein Genes and Agronomic Genes

In certain embodiments, methods and transgenic plants disclosed herein facilitate production of a foreign protein or polypeptide in commercial quantities. For example, harvesting of a plurality of transgenic plants in a conventional manner, and extraction of the foreign protein or polypeptide from a tissue of interest or from total biomass can be carried out. Protein extraction from plant biomass can be accomplished by known methods which are discussed, for example, by Heney and Orr, *Anal. Biochem.* 114: 92-6 (1981).

In one embodiment, the transgenic plant provided for commercial production of foreign protein is sunflower. In one embodiment, the biomass of interest is seed. For the relatively small number of transgenic plants that show higher levels of expression, a genetic map can be generated, for example via conventional Restriction Fragment Length Polymorphisms (RFLP), Polymerase Chain Reaction (PCR) analysis, and Simple Sequence Repeats (SSR). These techniques can be used to identify the approximate chromosomal location of the integrated DNA molecule. Map information concerning chromosomal location can be used in methods which protect the proprietary genetic information of a subject transgenic plant. If unauthorized propagation is undertaken and crosses made with other germplasm, the map of the integration region can be compared to similar maps for suspect plants, to determine if the latter have a common parentage with the subject plant. Map comparisons can be carried out using conventional techniques, for example, hybridizations, RFLP, PCR, SSR and sequencing.

In certain embodiments, agronomic genes can be expressed in transformed plants as described below.

Insect- and Disease-Related Traits

Insect-related or disease-related genes and proteins include for example *Bacillus thuringiensis* protein, a derivative thereof or a synthetic polypeptide modeled thereon; a lectin, a vitamin-binding protein, such as avidin; an enzyme inhibitor, for example, a protease inhibitor or an amylase inhibitor; an insect-specific hormone or pheromone such as an ecdysteroid and juvenile hormone, a variant thereof, a mimetic based thereon, or an antagonist or agonist thereof; an insect-specific venom, peptide or neuropeptide which, upon expression, disrupts the physiology of the affected pest. See e.g., U.S. Pat. No. 5,266,317 to Tomalski et al., which disclosure is herein incorporated by reference in its entirety; an enzyme responsible for an hyperaccumulation of a monterpene, a sesquiterpene, a steroid, hydroxamic acid, a phenylpropanoid derivative or another non-protein molecule with insecticidal activity; an enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197, which discloses the nucleotide sequence of a callase gene. Other examples include signal transduction sequences such as mung bean or maize calmodulin, hydrophobic moment peptides such as Tachyplesin (see PCT application WO95/16776) and other synthetic antimicrobial peptides (see PCT application WO95/18855), membrane permeases, including channel formers and a channel blockers, such as cecropin-β lytic peptide, viral-invasive proteins or a complex toxins derived therefrom, to confer resistance to, for example, alfalfa mosaic virus, cucumber mosaic virus, tobacco streak virus, potato virus X, potato virus Y, tobacco etch virus, tobacco rattle virus and tobacco mosaic virus, insect-specific antibodies or an immunotoxins derived therefrom, virus-specific antibodies and developmental-arrestive proteins such as fungal endo α-1,4-D-polygalacturonases, bean endopolygalacturonase-inhibiting protein, and ribosome-inactivating gene.

Herbicide-Related Traits

Resistance to a herbicide that inhibits the growing point or meristem, such as an imidazalinone or a sulfonylurea may be introduced, for example, using coding sequences for mutant ALS and AHAS enzymes. Other targets include glyphosate (resistance imparted by mutant 5-enolpyruvl-3-phosphikimate synthase (EPSP) and aroA genes) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSP which can confer glyphosate resistance. The nucleotide sequence of the mutant aroA gene is disclosed in U.S. Pat. No. 4,769,061 to Comai. U.S. Pat. No. 4,975,374 to Goodman et al. discloses nucleotide sequences of glutamine synthetase genes which confer resistance to herbicides such as L-phosphinothricin. Glutathione S-transferase, Phosphinothricin-acetyl-transferase gene, and expression of chimeric bar genes coding for phosphinothricin acetyl transferase activity can also be used. Genes conferring resistance to phenoxy proprionic acids and cycloshexones, such as sethoxydim and haloxyfop, such as the Acc1-S1, Acc1-S2 and Acc1-S3 genes may also be used.

Photosynthesis-inhibiting herbicides, such as a triazine (psbA and gs+ genes) and a benzonitrile (nitrilase gene) can also be targets. Nucleotide sequences for nitrilase genes are disclosed in U.S. Pat. No. 4,810,648 to Stalker.

Conferment or Contribution to a Value-Added Trait

Value-added traits which may be targets include modified fatty acid metabolism, for example, by reducing expression of stearoyl-ACP desaturase to increase stearic acid content, decreased phytate content, such as by introducing a phytase-encoding gene, modified carbohydrate or oil composition effected, for example, by transforming plants with a gene coding for an enzyme that alters the branching pattern of starch or which increases or decreases the amount or type of fatty acid in oil.

Methods for Sunflower Transformation

Numerous methods for sunflower plant transformation can be used, including biological and physical plant transformation protocols, such as *Agrobacterium*-mediated transformation and direct gene transfer. See, for example, Knittel et al., "Transformation of *Sunflower/Helianthus annuus* L.) A Retrievable Protocol", *Plant Cell Rep.* 14:81-86; Malone-Schoneberg, J., et al. 1994, "Stable Transformation of Sunflower Using *Agrobacterium* and Split Embryonic Axis Explants", *Plant Science,* 103:119-207. Following transformation of sunflower target tissues, such as described herein, expression of selectable marker genes allows for preferential selection of transformed cells, tissues and/or plants, using regeneration and selection methods known in the art.

Several sunflower transformant protocols can be used which allow for the identification of transformants without the need for selectable markers. For example, Nutler et al. 1987, "Factors Affecting the Level of Kanamycin Resistance in Transformed Sunflower Cells", *Plant Physiol.* 84:1185-1192. See also, Bidney, D., et al., supra, which use intact meristem explants and analyze gene expression in leaf tissue via protein methods such as ELISA or enzyme assay or nucleic acid methods such as PCR or RT-PCR.

In certain embodiments, the foregoing methods for transformation are used for producing transgenic inbred lines. Transgenic inbred lines can be crossed with another line, for example, a non-transformed or transformed inbred line, in order to produce a transgenic hybrid sunflower plant. In certain embodiments, a genetic trait which has been engineered or introduced into a particular sunflower line or sunflower plant cell using the transformation techniques such as described herein can be moved into another line using traditional backcrossing techniques known in the plant breeding arts. For example, a backcrossing approach can be used to move an engineered trait from a non-elite line into an elite line, or from a hybrid sunflower plant containing a foreign gene in its genome into a line or lines which do not contain that gene. As used herein, "crossing" can refer to a simple X by Y forward cross, or the process of backcrossing, depending on the context.

Seed Treatment, Conditioning and Cleaning

Methods for cleaning, conditioning or treating seed and the seed so cleaned or treated are provided. Cleaning the seed includes removing foreign debris such as weed seed and removing chaff and plant matter, from the seed. Conditioning the seed can include controlling the temperature and rate of dry down and storing seed in a controlled temperature environment. Seed treatment is the application of a composition to the seed such as a coating or powder. Some examples of compositions are insecticides, fungicides, pesticides, antimicrobials, germination inhibitors, germination promoters, cytokinins, and nutrients.

Methods for Analyzing Polynucleotides

Methods for analyzing a polynucleotide from plants, plant parts or seeds described herein may include contacting a polynucleotide from the plant, plant part or seed, such as from hybrid sunflower variety PH1023B with a molecular marker or with modified nucleotides that facilitate sequencing of the polynucleotide. The polynucleotide may be isolated, separated or otherwise obtained from the plant, plant part or seed. Modified nucleotides such as dNTPs may be incorporated with the polynucleotides along with appropriate primers in a reaction mixture that facilitates sequencing. Sequencing can be done using any method known in the art.

It will be apparent to those of skill in the art that variations may be applied to the compositions and methods described herein and in the steps or in the sequence of steps of the method described herein without departing from the concept, spirit and scope of the invention. More specifically, it will be apparent that certain changes and modifications such as single gene conversions, including for example, modifications and mutations, somoclonal variants, variant individuals selected from large populations of the plants of the instant inbred and the like may be practiced. All such similar substitutes and modifications apparent to those skilled in the art are deemed to be within the spirit, scope and concept of the invention.

It is to be understood that the invention is not limited in its application to the details of construction and the arrangement of components set forth in the following description. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. All publications, patents and patent applications are herein expressly incorporated by reference in their entirety for all purposes to the same extent as if each individual publication or patent application was specifically and individually incorporated by reference. In case of conflict between the present disclosure and the incorporated patents, publications and references, the present disclosure should control.

Deposits

Applicant has made a deposit of at least 2,500 seeds of Inbred Sunflower Line PH1023B with the American Type Culture Collection (ATCC), 10801 University Boulevard, Manassas, Va. 20110-2209, USA, with ATCC Deposit No. PTA-122855. The seeds deposited with the ATCC on Feb. 24, 2016 were obtained from the seed of the variety maintained by Pioneer Hi-Bred International, Inc., 7250 NW 62nd Avenue, Johnston, Iowa, 50131 since prior to the filing date of this application. Access to this seed will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. §1.808. This deposit of the Inbred Sunflower Line PH1023B will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all of the requirements of 37 C.F.R. §§1.801-1.809, including providing an indication of the viability of the sample upon deposit. Applicant has no authority to waive any restrictions imposed by law on the transfer of biological material or its transportation in commerce. Applicant does not waive any infringement of rights granted under this patent or under the Plant Variety Protection Act (7 USC 2321 et seq.).

What is claimed is:

1. A seed, plant, plant part, or plant cell of sunflower inbred line PH1023B, representative seed of the line having been deposited under ATCC accession number PTA-122855.

2. A sunflower plant, plant part, or plant cell, produced by growing the seed of claim 1.

3. The sunflower plant of claim 2, wherein the plant is male sterile.

4. A tissue culture of regenerable cells from the plant of claim 2.

5. A sunflower plant regenerated from the tissue culture of claim 4, capable of expressing all the morphological and physiological characteristics of inbred line PH1023B, representative seed of the inbred line PH1023B having been deposited under ATCC accession number PTA-122855.

6. A method for producing a hybrid sunflower seed comprising crossing the plant of claim 2 with a different inbred parent sunflower plant and harvesting the resultant first generation ($F_1$) hybrid sunflower seed.

7. An $F_1$ hybrid seed produced by crossing the inbred sunflower plant according to claim 2 with another, different sunflower plant.

8. An $F_1$ hybrid plant, or parts thereof, grown from the seed of claim 7, wherein the plant parts are selected from the group consisting of plant cells, plant protoplasts, plant calli, leaves, stems, stalks, cortex, pith, involucral bracts, ray flowers, disk flowers, interfloral bracts, receptacles, stigma, anthers, styles, filaments, calyx, roots, root tips, anthers, silks and combinations thereof.

9. The sunflower plant, plant part, or plant cell, of claim 2, wherein the plant, plant part, or cell has been transformed so that its genetic material contains one or more transgenes operably linked to one or more regulatory elements.

10. A method for producing a sunflower plant that contains in its genetic material one or more transgenes, comprising crossing the sunflower plant of claim 9 with (i) a second plant of a second sunflower line, (ii) a non-transformed sunflower plant of the line PH1023B, or (iii) a different transformed plant of the line PH1023B, such that the genetic material of the progeny of the cross contains the one or more transgenes operably linked to one or more regulatory element.

11. Sunflower plants, plant parts, or plant cells produced by the method of claim 10.

12. A method for developing a sunflower plant in a sunflower plant breeding program, comprising applying plant breeding techniques to the plant, or plant parts of claim 2 to produce a second sunflower plant.

13. The sunflower plants, plant parts, or plant cells of claim 2, further comprising one or more single gene conversions introduced into inbred sunflower line PH1023B through backcrossing or transformation, wherein the plants, and plants grown from the plant parts and plant cells, otherwise have all the morphological and physiological characteristics recited in Table 1.

14. A sunflower plant having all the physiological and morphological characteristics of the plant of claim 1.

15. A method for producing inbred PH1023B, representative seed of which have been deposited under ATCC accession number PTA-122855, comprising:
 (a) planting a collection of seed comprising seed of a hybrid, one of whose parents is inbred PH1023B the collection also comprising seed of the inbred;
 (b) growing plants from the collection of seed;
 (c) identifying the inbred PH1023B plants;
 (d) selecting the inbred PH1023B plant; and
 (e) controlling pollination in a manner which preserves the homozygosity of the inbred PH1023B plant.

16. A method for producing a PH1023B-derived sunflower plant, comprising:
 (a) crossing inbred sunflower line PH1023B, representative seed of the line having been deposited under ATCC accession number PTA-122855, with a second sunflower plant to yield progeny sunflower seed;
 (b) growing the progeny sunflower seed, under plant growth conditions, to yield the PH1023B-derived sunflower plant.

17. The method of claim 16, further comprising:
 (c) crossing the PH1023B-derived sunflower plant with itself or another sunflower plant to yield additional PH1023B-derived progeny sunflower seed;
 (d) growing the progeny sunflower seed of step (c) under plant growth conditions, to yield additional PH1023B-derived sunflower plants;
 (e) repeating the crossing and growing steps of (c) and (d) from 0 to 5 times to generate further PH1023B-derived sunflower plants.

18. The method of claim 16, further comprising utilizing plant tissue culture methods to produce progeny of the PH1023B-derived sunflower plant.

19. A method for producing a hybrid sunflower seed comprising crossing the plant of claim 13 with a different inbred parent sunflower plant and harvesting the resultant first generation ($F_1$) hybrid sunflower seed.

20. A method for producing polynucleotides, the method comprising isolating polynucleotides from the seed, plant or plant part of claim 1.

\* \* \* \* \*